United States Patent [19]

Savins et al.

[11] 4,079,182

[45] Mar. 14, 1978

[54] HEXAMETHYLENETETRAMINIUM COMPOUNDS

[75] Inventors: Eric George Savins, Maidenhead; Philip David Bentley, Bracknell, both of England

[73] Assignee: Imperial Chemical Industries Limited, London, England

[21] Appl. No.: 739,194

[22] Filed: Nov. 5, 1976

[30] Foreign Application Priority Data

Nov. 11, 1975 United Kingdom ............... 46555/75

[51] Int. Cl.² ........................................... C07D 295/02
[52] U.S. Cl. ................................. 544/185; 260/600 R
[58] Field of Search ...................... 260/248.5; 544/185

[56] References Cited

U.S. PATENT DOCUMENTS

| | | | |
|---|---|---|---|
| 3,228,829 | 1/1966 | Wolf et al. ..................... | 260/248.5 X |
| 3,574,209 | 4/1971 | Suter et al. ..................... | 260/248.5 |
| 3,624,253 | 3/1970 | Pawloski .......................... | 260/248.5 |

*Primary Examiner*—John M. Ford
*Attorney, Agent, or Firm*—Cushman, Darby & Cushman

[57] ABSTRACT

Quaternary ammonium salts consisting of cations and anions wherein the cations have the formula:

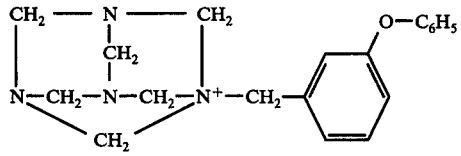

and the anions are halide ions. These salts which are useful as intermediates in the preparation of 3-phenoxybenzaldehyde, may be prepared by reacting a 3-phenoxybenzyl halide with hexamethylenetetramine.

3 Claims, No Drawings

HEXAMETHYLENETETRAMINIUM COMPOUNDS

This invention relates to novel quaternary ammonium salts useful in the preparation of intermediates for insecticides.

Accordingly the invention provides quaternary ammonium salts having a cation of formula:

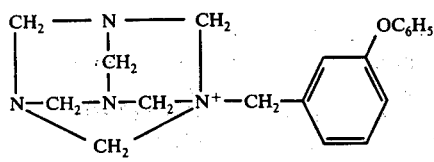

in association with an anion. Preferably the anion is a halide ion, for example a chloride or bromide ion. Salts with other anions are possible and may be prepared by for example ion exchange techniques from the halides.

The quaternary ammonium salt of the invention may be names as N-(3-phenoxybenzyl)hexamethylenetetraminium salts, for example N-(3-phenoxybenzyl)hexamethylenetetraminium bromide, and N-(3-phenoxybenzyl)hexamethylenetetraminium chloride.

The quaternary ammonium salts of the invention may be prepared by reacting a 3-phenoxybenzyl halide with hexamethylenetetramine. The reaction is conveniently carried out in a diluent in which the reactants are soluble and in which the quaternary salt is substantially insoluble, for example a liquid chlorinated hydrocarbon diluent. Chlorinated hydrocarbon diluents having a molecular weight in the range 80 to 250 are particularly suitable, for example, methylene chloride, chloroform, carbon tetrachloride, ethylene dichloride and trichloroethane.

The reaction can be carried out at temperatures within the range from about 0° C to the reflux temperature of the diluent, but a temperature within the range from about 25° C to about 70° C is particularly preferred. The reaction may be commenced at one temperature, for example the ambient temperature, and concluded at another, higher, temperature. The application of heat to the reaction mixture serves to accelerate and complete the reactions involved. The period of reaction may be varied depending on the conditions used, but in general a period of from about 30 minutes to about 10 hours will afford a good yield of the product.

The quaternary ammonium salts of the invention are useful as intermediates in the production of 3-phenoxybenzaldehyde.

3-Phenoxybenzaldehyde is a useful intermediate in the preparation of insecticides. Upon reduction with, for example aluminium isopropoxide under the conditions of the Wagner-Meerwein-Ponndorf Reaction, it may be converted to 3-phenoxybenzyl alcohol, esters of which with certain acids, e.g. chrysanthemic acids, are known insecticides. A particularly useful insecticidal ester is 3-phenoxybenzyl 2(2,2-dichlorovinyl)-3,3-dimethylcyclopropane carboxylate.

Insecticidal esters are also obtained from the cyanhydrin of 3-phenoxybenzaldehyde and certain acids. Particular mention may be made of α-cyano-3-phenoxybenzyl 2(2,2-dichlorovinyl)-3,3-dimethylcyclopropane carboxylate, and α-cyano-3-phenoxybenzyl 2(4-chlorophenyl) isovalerate.

In a further aspect therefore the invention provides a process for the preparation of 3-phenoxybenzaldehyde which comprises the step of contacting a quaternary ammonium salt of the invention as defined hereinabove with an aqueous solution of a mineral acid or an organic carboxylic acid.

The process is preferably conducted at an elevated temperature, within the range 50° C to 110° C. Examples of useful acids are acetic acid, preferably in the form of a concentrated aqueous solution, containing from 30 to 70% by weight of the acid, or hydrochloric acid. The acids are preferably used in excess. The temperature at which this step of the process is carried out is conveniently the reflux temperature of the reaction mixture. The product, 3-phenoxybenzaldehyde, may be isolated by extraction with a suitable solvent, for example chloroform.

In a variation of the above process the quaternary ammonium salt may be prepared in situ in the aqueous acid medium used to prepare the 3-phenoxybenzaldehyde, by the reaction between 3-phenoxybenzyl halide and hexamethylene tetramine.

The invention is illustrated by the following Examples.

EXAMPLE 1

This Example illustrates the preparation of the N-(3-phenoxybenzyl)hexamethylenetetraminium bromide.

3-Phenoxybenzyl bromide (2.0 g) was carefully added to a stirred solution of hexamethylene tetramine (2.1 g) in carbon tetrachloride (20 ml) at the ambient temperature. The precipitate which formed was collected after a period of five minutes by filtration and washed with acetone to yield N-(3-phenoxybenzyl)hexamethylenetetraminium bromide.

EXAMPLE 2

This Example illustrates the preparation of N-(3-phenoxybenzyl)hexamethylenetetraminium chloride.

3-Phenoxybenzyl chloride (21.9 g) was added dropwise to a refluxing solution of hexamethylene tetramine (15.4 g) in chloroform (120 ml), and the mixture refluxed for 2 hours. After cooling to the ambient temperature the precipitate was collected by filtration, and washed with a little cold chloroform to yield N-(3-phenoxybenzyl)hexamethylenetetraminium chloride, m.p. 178°-185° C (decomposition).

EXAMPLE 3

This Example illustrates the preparation of 3-phenoxybenzaldehyde from N-(3-phenoxybenzyl)hexamethylenetetraminium chloride.

A mixture of N-(3-phenoxybenzyl)hexamethylenetetraminium chloride (17.9 g), hexamethylene tetramine (7.0 g), glacial acetic acid (25 ml) and water (25 ml) was refluxed for 2 hours, after which concentrated hydrochloric acid (20 ml) was added to the cooled mixture. The mixture was shaken with dichloromethane (50 ml) and the organic phase separated, washed with water, dried over anhydrous magnesium sulphate, and evaporated under reduced pressure to yield 3-phenoxybenzaldehyde as a pale yellow oil, identified by comparison with an authentic sample.

EXAMPLE 4

This Example illustrates the preparation of 3-phenoxybenzaldehyde by a process involving the in situ preparation of N-(3-phenoxybenzyl)hexamethylenetetraminium chloride.

Hexamethylene tetramine (14.0 g) was added to a mixture of 3-phenoxybenzyl chloride (10.9 g), glacial acetic acid (25 ml) and water (25 ml) under a nitrogen atmosphere and the mixture refluxed for 2.5 hours, after which concentrated hydrochloric acid (20 ml) was added and the refluxing continued for a further 15 minutes. The mixture was cooled to the ambient temperature, extracted with diethyl ether and the extracts washed with water, saturated sodium bicarbonate solution, and finally with water. After drying the ethereal solution over anhydrous magnesium sulphate, the ether was evaporated under reduced pressure to yield 3-phenoxybenzaldehyde, identified by comparison with an authentic sample.

We claim:

1. A quaternary ammonium salt consisting of cations and anions wherein the cations have the formula:

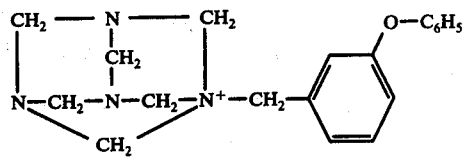

and the anions are halide ions.

2. A quaternary ammonium salt according to claim 1 wherein the anions are chloride ions.

3. A quaternary ammonium salt according to claim 1 wherein the anions are bromide ions.